US011147917B2

(12) United States Patent
Wolff

(10) Patent No.: US 11,147,917 B2
(45) Date of Patent: Oct. 19, 2021

(54) INFUSION DEVICE FOR ADMINISTERING A MEDICAL FLUID TO A PATIENT AND METHOD FOR OPERATING AN INFUSION DEVICE

(71) Applicant: Fresenius Vial SAS, Brézins (FR)

(72) Inventor: Rémy Wolff, Morette (FR)

(73) Assignee: Fresenius Vial SAS, Brézins (FR)

(*) Notice: Subject to any disclaimer, the term of this patent is extended or adjusted under 35 U.S.C. 154(b) by 515 days.

(21) Appl. No.: 15/757,908

(22) PCT Filed: Sep. 30, 2016

(86) PCT No.: PCT/EP2016/073385
§ 371 (c)(1),
(2) Date: Mar. 6, 2018

(87) PCT Pub. No.: WO2017/060166
PCT Pub. Date: Apr. 13, 2017

(65) Prior Publication Data
US 2020/0030526 A1 Jan. 30, 2020

(30) Foreign Application Priority Data
Oct. 5, 2015 (EP) .................................... 15306557

(51) Int. Cl.
*A61M 5/14* (2006.01)
*A61M 5/145* (2006.01)
*A61M 5/20* (2006.01)

(52) U.S. Cl.
CPC ...... *A61M 5/14546* (2013.01); *A61M 5/1456* (2013.01); *A61M 5/20* (2013.01)

(58) Field of Classification Search
CPC ............ A61M 5/14546; A61M 5/1456; A61M 5/1452; A61M 5/14216
See application file for complete search history.

(56) References Cited
U.S. PATENT DOCUMENTS 4,191,187 A * 3/1980 Wright ................ A61M 5/1456
604/155
5,006,112 A 4/1991 Metzner
(Continued)

FOREIGN PATENT DOCUMENTS

| CN | 1433816 | 8/2003 |
| CN | 104066464 | 9/2014 |
| WO | WO 2012/055771 A1 | 5/2012 |

OTHER PUBLICATIONS

International Search Report and Written Opinion, counterpart International Appl. No. PCT/EP2016/073385 dated Jan. 3, 2017 (14 pages).

*Primary Examiner* — Nathan R Price
*Assistant Examiner* — Courtney B Fredrickson
(74) *Attorney, Agent, or Firm* — Cook Alex Ltd.

(57) ABSTRACT

An Infusion device (1) for administering a medical fluid to a patient, comprises: a housing (10); a receptacle (11) arranged on the housing (10) for receiving a syringe (2); a pusher device (12) movable in a pushing direction (P) for acting onto a piston (21) of a syringe (2) received on the receptacle (11); a drive element (13) connected to the pusher device (12), the drive element (13) being longitudinally movable relative to the housing (10) for moving the pusher device (12) along the pushing direction (P); a driving rod (14) having a screw thread (140) and being rotatable about a rotational axis (R1); an electric drive device (141) for rotating the driving rod (14); a clutching device (130) connected to the drive element (13) and being actuatable, by an actuation device (15), to engage, in a clutched state, with the screw thread (140) of the driving rod (14) for translating a rotational movement of the driving rod (14) into a longitudinal movement of the drive element (13) along the driving rod (14), and to disengage, in an unclutched state, from the driving rod (14); a brake device (16) constituted to (Continued)

act, in an activated state, onto the drive element (13) for braking the drive element (13) relative to the housing (10) and to allow, in a deactivated state, a longitudinal movement of the drive element (13) relative to the housing (10); a control device (17) to control the electric drive device (141) and the brake device (16); and a sensing device (170) for detecting an actuation state of the clutching device (130). Herein, the control device (17) is constituted, when the sensing device (170) detects that the clutching device (130) is actuated to change from the unclutched state to the clutched state, to perform a control sequence during which the control device (17) controls the electric drive device (141) to rotate the driving rod (14) for a predetermined duration or for a predetermined angle of rotation while the brake device (16) is in the activated state.

7 Claims, 5 Drawing Sheets

(56) References Cited

U.S. PATENT DOCUMENTS

| | | | |
|---|---|---|---|
| 5,106,375 A * | 4/1992 | Conero | A61M 5/1456 128/DIG. 1 |
| 2003/0149402 A1 | 8/2003 | Gerlach et al. | |
| 2004/0064088 A1 | 4/2004 | Gorman et al. | |
| 2007/0074596 A1 | 4/2007 | Siefert | |
| 2012/0215170 A1* | 8/2012 | Traversaz | A61M 5/14546 604/155 |
| 2014/0188076 A1 | 7/2014 | Kamen et al. | |
| 2014/0343533 A1 | 11/2014 | Gerlach et al. | |

\* cited by examiner

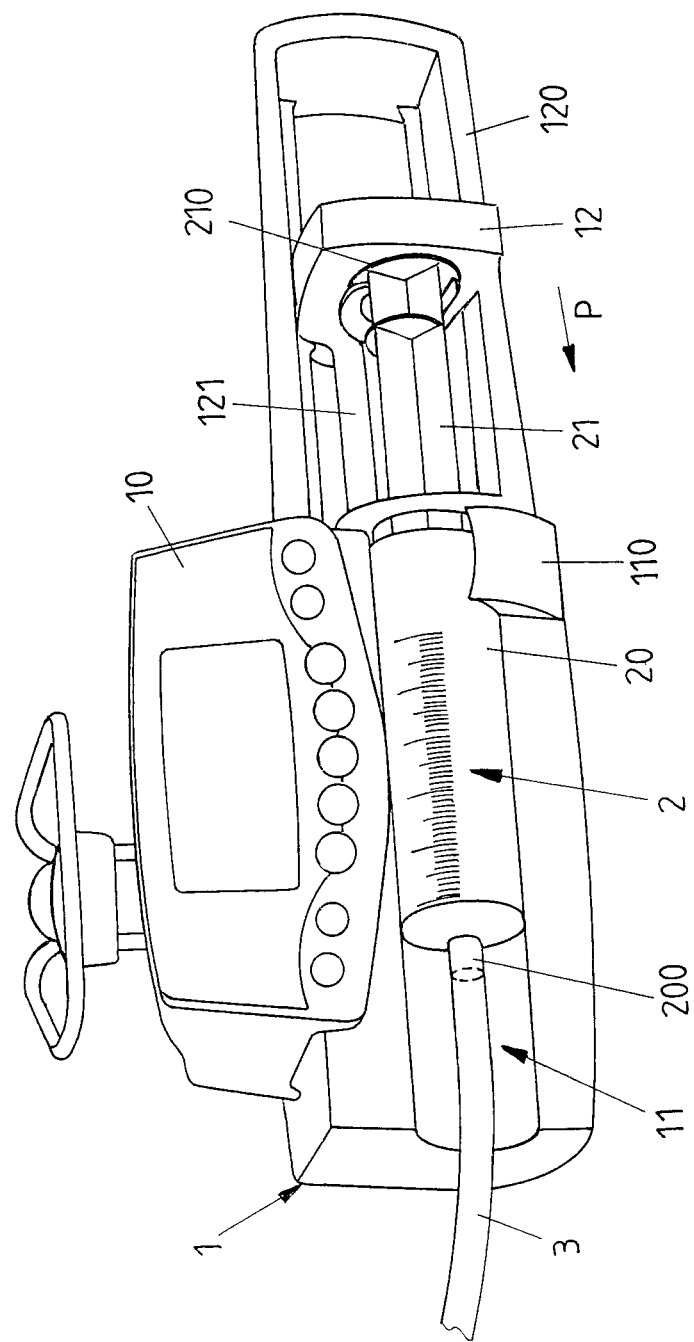

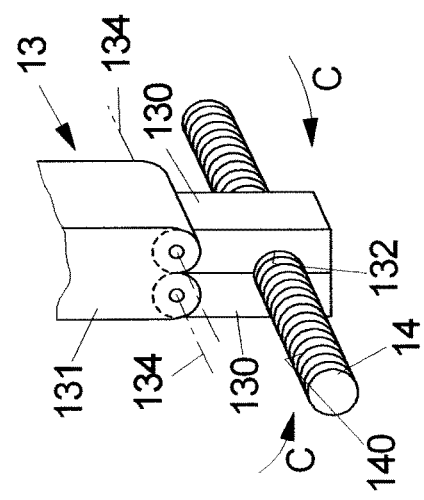
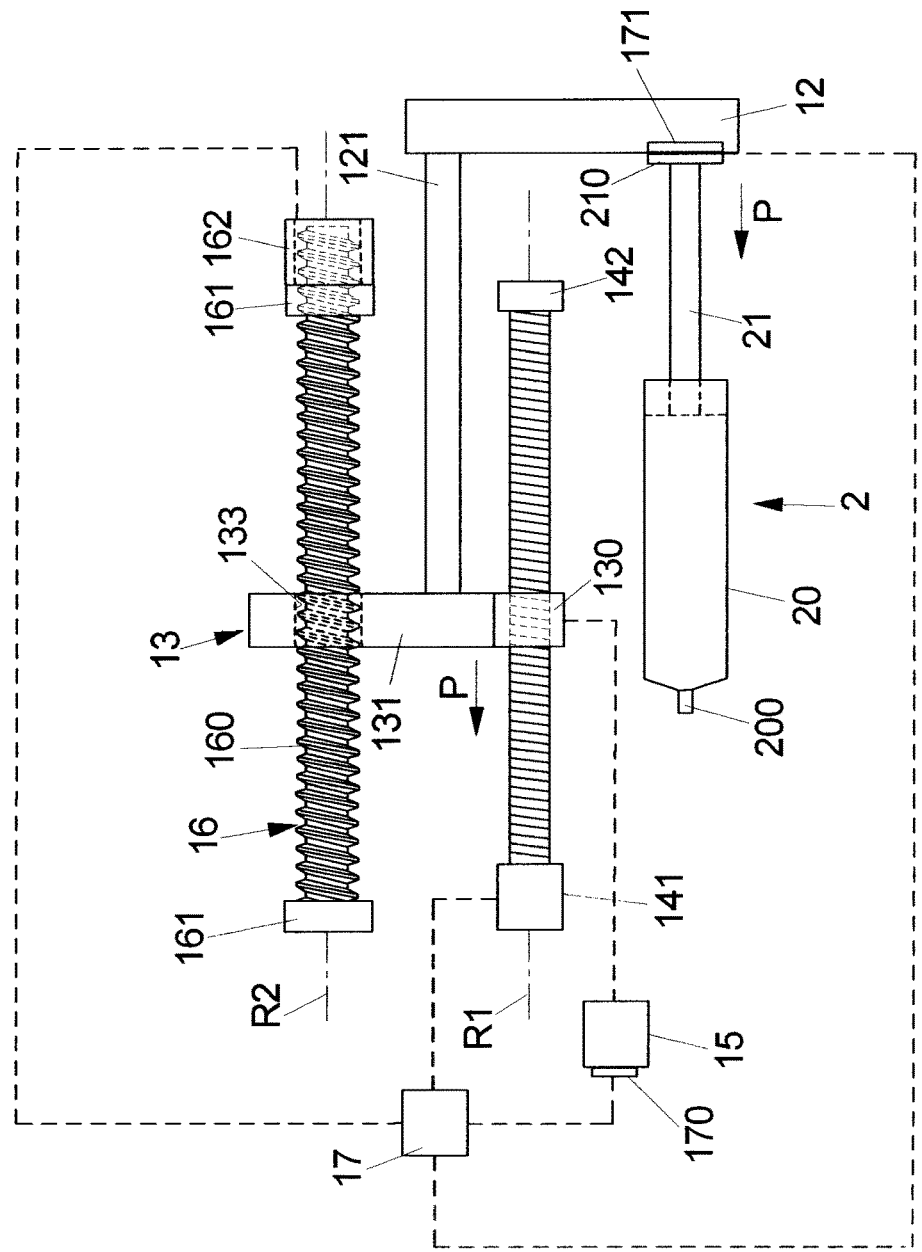

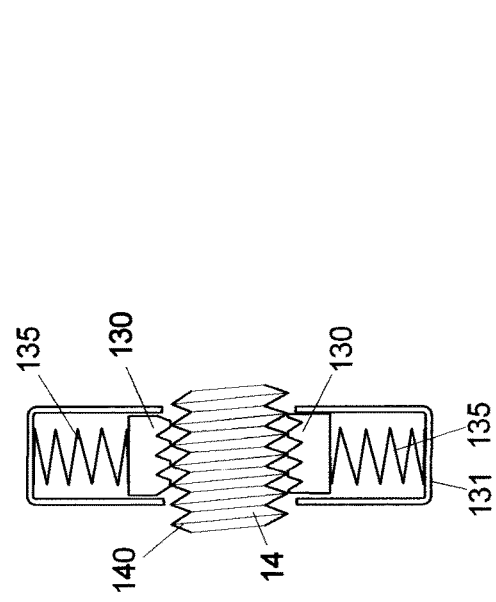
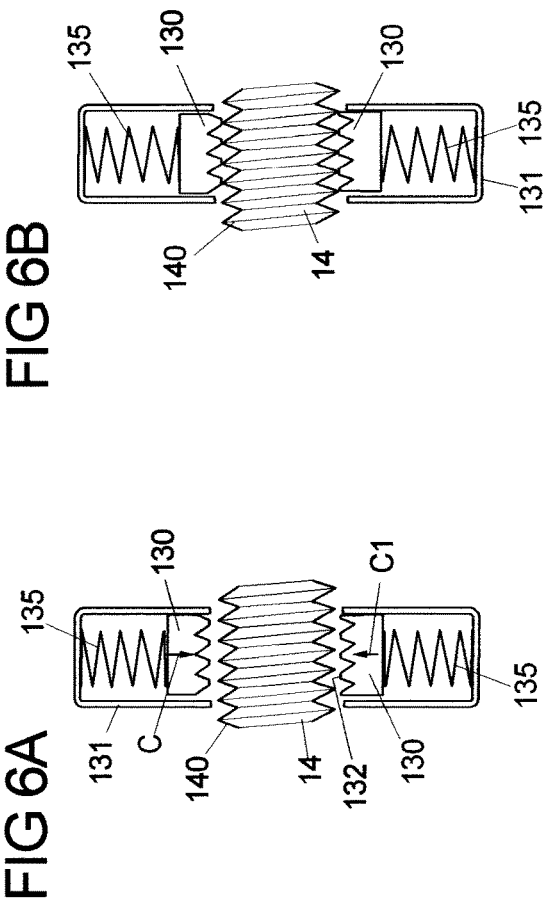
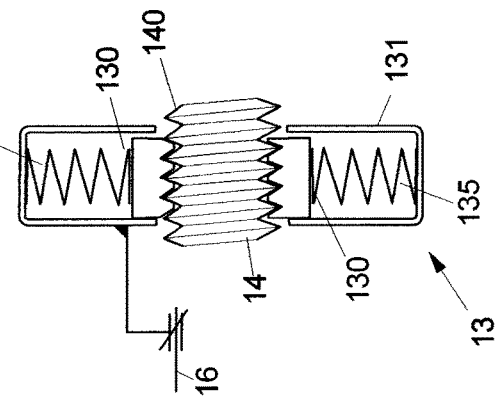
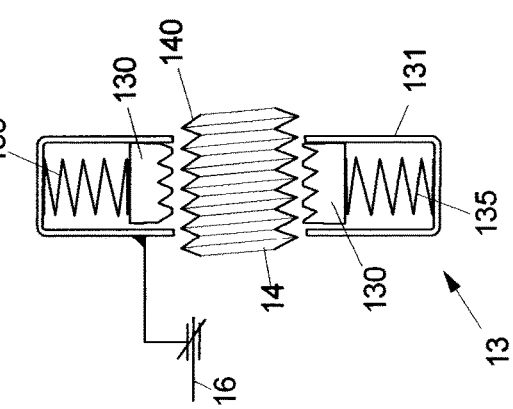
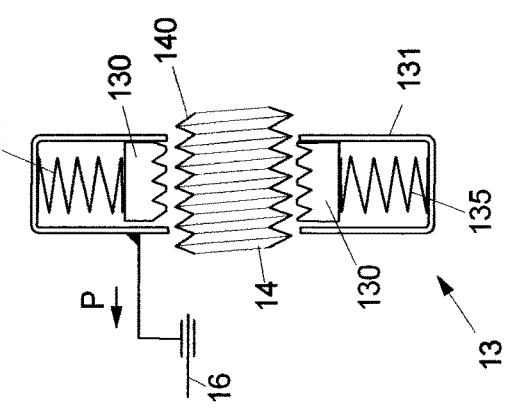

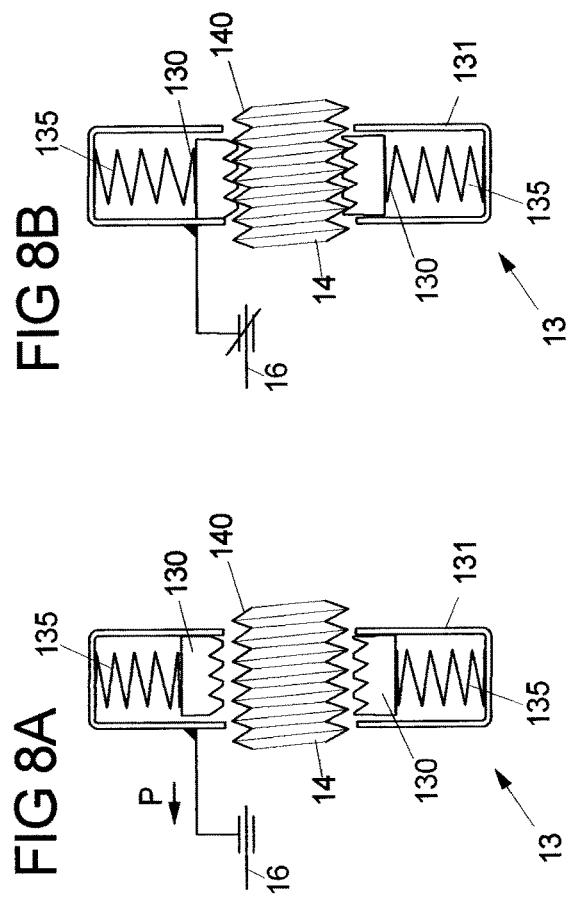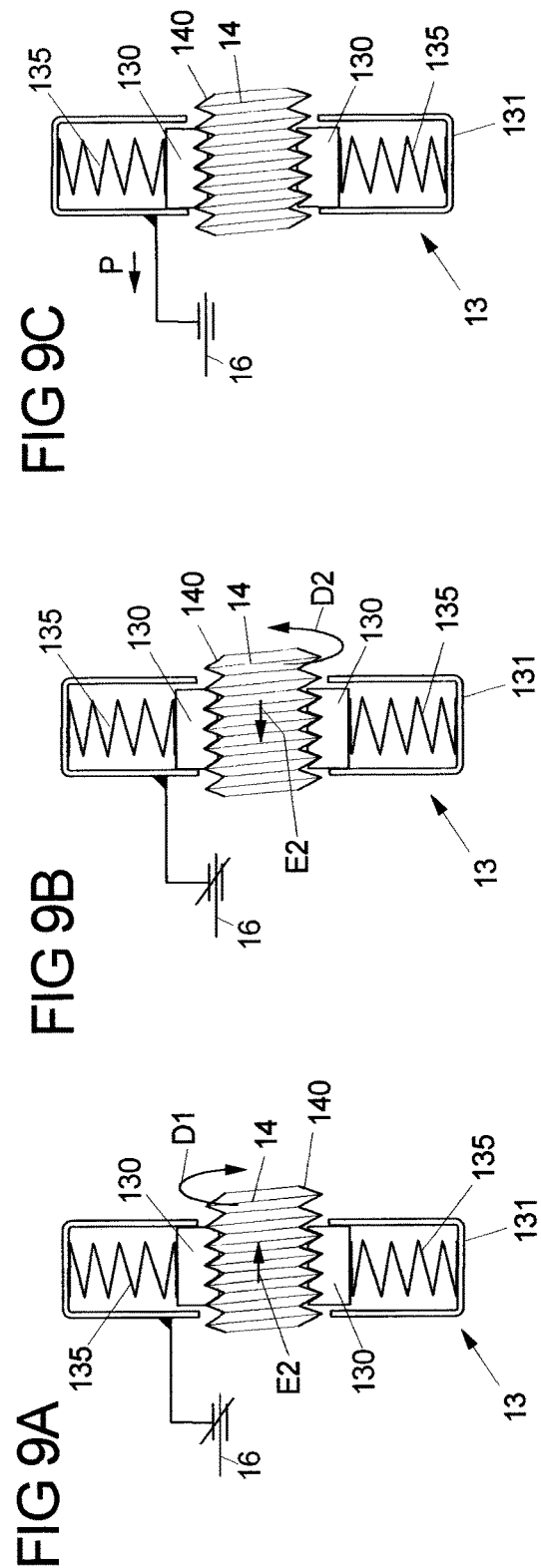

INFUSION DEVICE FOR ADMINISTERING A MEDICAL FLUID TO A PATIENT AND METHOD FOR OPERATING AN INFUSION DEVICE

The present application is a U.S. National Stage of PCT international Patent Application No. PCT/EP2016/073385, filed Sep. 30, 2016, which claims priority to EP Application No. 15306557, filed Oct. 5, 2015, both of which are hereby incorporated herein by reference The invention relates to an infusion device for administering a medical fluid to a patient according to the preamble of claim 1 and to a method for operating an infusion device.

An infusion device of this kind comprises a housing, a receptacle arranged on the housing for receiving a syringe, and a pusher device movable in a pushing direction for acting onto a piston of a syringe received on the receptacle. The infusion device is constituted as a syringe pump, the syringe containing a medical fluid to be infused to a patient. A medical fluid of this kind may for example be a medication, a solution for the parenteral feeding or another medical solution which shall be infused to a patient.

The pusher device is driven by a drive mechanism comprising a drive element connected to the pusher device. The drive element is longitudinally movable relative to the housing for moving the pusher device along the pushing direction and is driven by a driving rod having a screw thread. The driving rod is rotatable about a rotational axis and is in connection with an electric drive device serving to electrically rotating the driving rod.

The drive element is in engagement with the screw thread of the driving rod in a releasable fashion. For this, a clutching device is provided which is connected to the drive element and which is actuatable by an actuation device to engage, in a clutched state, with the screw thread of the driving rod for translating a rotational movement of the driving rod into a longitudinal movement of the drive element along the driving rod. In the clutched state, hence, the drive element is in operational connection with the driving rod such that the drive element is moved along the driving rod when the driving rod is rotated by means of the electric drive device. To release the drive element from the driving rod the clutching device can be brought into an unclutched state in which the clutching device is disengaged from the driving rod such that the drive element can be moved independently from the driving rod.

In addition, the infusion device comprises a brake device constituted to act, in an activated state, onto the drive element for braking the drive element relative to the housing and to allow, in a deactivated state, a longitudinal movement of the drive element relative to the housing. By means of the brake device the drive element can be held fixed such that the drive element cannot be freely moved relative to the housing even when the clutching device is in its unclutched state. During normal operation of the infusion device (when the drive element is driven by the driving rod to push onto a piston of a syringe) the brake device is in its deactivated state such that it does not hinder a movement of the drive element.

To control the operation of the infusion device a control device is provided which issues control commands for controlling the electric drive device as well as the brake device. In particular, the control device is operable to activate the electric drive device for rotating the driving rod and to switch the brake device between its activated state and its deactivated state. In addition, a sensing device serves to detect an actuation state of the clutching device, for example by detecting in which position the actuation device, for example a lever, currently is.

An infusion device of this kind is described in US 2012/0215170 A1, which shall in its entirety be incorporated herein by reference.

When installing a syringe on the receptacle of the housing, typically the clutching device is brought into its unclutched state such that the drive element and together with it the pusher device is freely movable relative to the driving rod. In this way, the pusher device can be moved towards a piston head of the piston of the syringe installed on the infusion device, such that the pusher device is brought into abutment with the piston head to be able to perform an infusion operation by pushing the piston into a cylindrical tube of the syringe. To bring the infusion device into an operative state, the clutching device is then transferred into the clutched state by accordingly actuating the actuation device, for example a lever, such that the clutching device engages with the screw thread of the driving rod. By rotating the driving rod, the drive element can then be longitudinally moved along the driving rod, and with it the pusher device is moved in the pushing direction in order to push onto the piston of the syringe.

Because the screw thread of the driving rod has a defined pitch, for example between 0.5 mm and 2 mm, for example 1 mm, the engagement of the clutching device with the screw thread of the driving rod may—in conventional infusion devices—lead to a (small) movement of the drive element relative to the driving rod, because the clutching device has to slide into engagement with the screw thread of the driving rod. Such horizontal movement may lead to the pusher device being removed from the piston head of the piston by a small margin, which may cause a delay during the start-up of an infusion process. Or this may lead to the pusher device being pushed against the piston head of the piston, such that an unwanted bolus may arise. In particular in cases where medication shall be infused at a very constant infusion rate, such bolus may have non-desirable effect on a patient.

It hence is an object to provide an infusion device and a method for operating an infusion device which allow for a reduction of an unwanted movement of the drive element relative to the driving rod when transferring the clutching device into its clutched state.

This object is achieved by means of an infusion device comprising the features of claim 1.

Accordingly, the control device is constituted, when the sensing device detects that the clutching device is actuated to change from the unclutched state to the clutched state, to perform a control sequence during which the control device controls the electric drive device to rotate the driving rod for a predetermined duration or for a predetermined angle of rotation while the brake device is in the activated state.

The control device hence is constituted to perform a control sequence once the clutching device changes from its unclutched state to its clutched state. If it is detected that the clutching device is actuated to engage with the screw thread of the driving rod and thus is transferred to its clutched state, the control device issues a control command to cause the electric drive device to rotate the driving rod for a predetermined duration or for a predetermined angle of rotation. This takes place while the brake device is in the activated state such that the drive element is fixedly held in position relative to the housing. The rotation of the driving rod hence causes a relative movement of the driving rod to the clutching device, which enables the clutching device to slide into engagement with the screw thread of the driving rod without a lateral movement of the drive element relative to the housing. Because the drive element is fixedly held in position by means of the brake device during the control sequence, the pusher device connected to the drive element cannot move during the control sequence, such that the pusher device is not moved relative to the piston head of the piston, avoiding a gap to occur in between the pusher device and the piston head and also avoiding an unwanted bolus.

The screw thread of the driving rod may for example have a pitch between 0.5 mm and 3 mm, for example 1 mm. The duration or the angle of rotation by which the driving rod is rotated during the control sequence may for example correspond to a movement of the driving rod for a lateral travel between 0.2 mm and 2 mm, for example 0.5 mm, i.e. a rotational movement of the driving rod corresponding to a lateral movement of the drive element between 0.2 mm and 2 mm, for example 0.5 mm. The predetermined duration may for example be less than 0.3 seconds.

The control sequence may for example be carried out when a syringe is installed on the infusion device, or after a manual bolus is performed by a user by pressing onto the pusher device and hence by moving the piston into the cylindrical tube of the syringe manually. During installation of a syringe or when performing a manual bolus the clutching device is in its unclutched state. After the installation is completed or after the manual bolus has been performed, the clutching device changes from its unclutched state to the clutched state, and on this occasion the control sequence may be carried out in order to ensure that the clutching device reliably and without unwanted movement of the drive element engages with the screw thread of the driving rod.

Generally, the control device may issue a control command to actuate the brake device to assume the activated state when the sensing device detects that the clutching device is actuated to change from the unclutched state to the clutched state. Hence, upon detecting that the clutching device is actuated to engage with the screw thread of the driving rod, the drive element is braked by means of the brake device in order to fixedly held the drive element in position relative to the housing.

This may in particular be suitable if a manual bolus is performed by a user. For performing a manual bolus, the user activates the clutching device to disengage from the driving rod such that the clutching device assumes the unclutched state. This enables the user to push onto the pusher device and to manually move the pusher device to perform the manual bolus. If the infusion device shall again be reverted to its normal operational state, the clutching device is actuated to engage with the driving rod and hence is transferred into its clutched state, which is detected by the sensing device and which causes the brake device to be activated such that the drive element is fixedly held in position relative to the housing for performing the control sequence.

The infusion device, in one embodiment, comprises a another, second sensing device constituted to detect an abutment of the pusher device with the piston of the syringe. The second sensing device may for example be constituted by a force sensor, a contact sensor such as a mechanical switch, or by another sensing device suitable to detect whether the pusher device abuts with the piston of the syringe installed on the infusion device.

In one aspect, the control device may be constituted to actuate the brake device to assume the activated state when the second sensing device detects that the pusher device has come into abutment with the piston. This may in particular be practical during installation of a syringe on the infusion device. During installation of the syringe the cylindrical tube of the syringe is installed in the receptacle on the housing of the infusion device, and subsequently the pusher device is moved to approach the piston of the syringe until the pusher device comes into abutment with the piston. Once it is detected that the pusher device has made contact with the piston, the brake device is caused to transition into its activated state such that the drive element is held in position relative to the housing. If now the clutching device is actuated to assume its clutched state and hence to engage with the screw thread of the driving rod, the control sequence may be carried out in order to ensure a reliable engagement of the clutching device with the driving rod without an unwanted movement of the drive element relative to the driving rod.

In one embodiment, the control device may be constituted, within the context of the control sequence, to control the electric drive device to rotate the driving rod first in a first rotational direction for a first predetermined duration or for a first predetermined angle of rotation and to subsequently rotate the driving rod in a second rotational direction opposite the first rotational direction for a second predetermined duration or for a second predetermined angle of rotation. For example, the driving rod may first be rotated backwards in a direction which would normally cause the drive element to be moved opposite to the pushing direction, and subsequently the driving rod may be rotated in a forward direction corresponding to a direction which would normally move the drive element (if fully engaged with the driving rod) forward in the pushing direction. By this it can be ensured that the drive element may reliably slide into engagement with the screw thread of the driving rod, and in addition a play between the clutching device and the drive element may be removed such that, upon subsequently starting a normal infusion operation, infusion is started at a desired infusion rate immediately without an undesirable delay.

For example, the driving rod may first be rotated backwards for a predetermined time or a predetermined angle of rotation corresponding to a travel between 0.2 mm and 2 mm, for example 0.5 mm (i.e. during normal operation of the infusion device the rotation of the driving rod would cause a movement of the drive element by this margin), and the driving rod may then be rotated for example for a predetermined duration or predetermined angle of rotation corresponding to a travel between 0.2 mm and 2 mm, for example 0.5 mm, in the other direction. The time of rotation may for example in each case be less than 0.3 seconds.

In one aspect, the control device is constituted to control the brake device to assume the deactivated state after the driving rod has been rotated. Hence, at the end of the control sequence the brake device is in the activated such that the drive element is released and may be moved relative to the housing.

The brake device may for example be constituted by an electromagnetic brake and may be connected to the drive element by a threaded spindle, as it is described in an specific embodiment in US 2012/0215170 A1, which shall be incorporated by reference herein.

The clutching device may, in one embodiment, comprise a pair of clutch elements which are movably arranged on the drive element and which each comprise a screw thread for engaging with the screw thread of the driving rod. The clutch elements may for example be shaped by a pair of half nuts, as described in US 2012/0215170 A1, and may be pivotably arranged on a frame member of the drive element. For engaging with the screw thread of the driving rod, the clutch elements are pivoted to approach each other such that they both engage, with their screw thread, with the screw thread of the driving rod. To unclutch the clutch elements from the driving rod the clutch elements are pivoted away from one another, such that the engagement between the clutch elements and the driving rod is released and the drive element is no longer operatively connected to the driving rod.

In another aspect, in a method for operating an infusion device for administering a medical fluid to a patient a syringe is received in a receptacle arranged on a housing of the infusion device, a pusher device is moved in a pushing direction for acting onto a piston of the syringe received on the receptacle, and a drive element connected to the pusher device is longitudinally moved relative to the housing for moving the pusher device along the pushing direction. For moving the drive element, a driving rod having a screw thread is rotated about a rotational axis by means of an electric drive device. Herein, a clutching device is provided connected to the driving element, the clutching device being actuatable by an actuation device to engage, in a clutched state, with the screw thread of the driving rod for translating a rotational movement of the driving rod into a longitudinal movement of the drive element along the driving rod, and to disengage, in an unclutched state, from the driving rod. In addition, a brake device is constituted to act, in an activated state, onto the drive element for braking the drive element relative to the housing and to allow, in a deactivated state, a longitudinal movement of the drive element relative to the housing. A control device controls the electric drive device and the brake device, and a sensing device detects an actuation state of the clutching state.

Herein, the control device performs, when the sensing device detects that the clutching device is actuated to change from the unclutched state to the clutched state, a control sequence during which the control device controls the electric drive device to rotate the driving rod for a predetermined duration or for a predetermined angle of rotation while the brake device is in the activated state.

The advantages and advantageous embodiments described above for the infusion device equally apply also to the method, such that it shall be referred to the above.

The idea underlying the invention shall subsequently be described in more detail with respect to the embodiments shown in the figures. Herein:

FIG. 1 shows a view of an embodiment of an infusion device in the shape of a syringe pump;

FIG. 2 shows a schematic view of a drive mechanism of the infusion device;

FIG. 3 shows a schematic view of a clutching device of a drive element of the drive mechanism;

FIG. 6A, 6B show a third situation while actuating the clutching device to assume the clutched state;

FIG. 7A to 7C show steps to be taken for transferring the clutching device into the clutched state during the installation of a syringe on the infusion device;

FIG. 8A, 8B show steps to be taken when transferring the clutching device to the clutched state after a manual bolus has been performed; and FIG. 9A to 9C show steps to be taken to perform a control sequence to engage clutch elements of the clutching device with a screw thread of a driving rod of the drive mechanism.

Figure 4A:
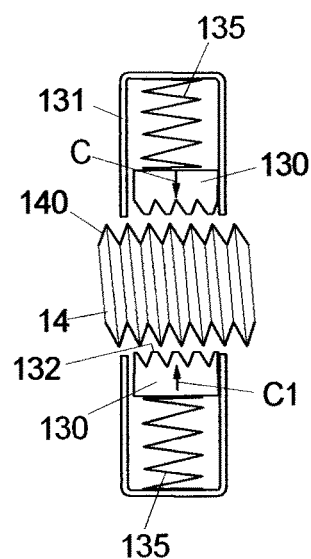
FIG. 4A to 4C show a first situation while actuating the clutching device to assume a clutched state.

FIG. 1 shows an infusion device 1 in the shape of a syringe pump having a housing 10 and a receptacle 11 arranged on the housing 10 to receive a syringe 2 therein.

The syringe 2 comprises a cylindrical tube 20 which, when installing the syringe 2 on the infusion device 1, contains a medical liquid, for example a medication or a solution for the parenteral feeding, to be infused to a patient. The cylindrical tube 20 is connected, via a connector 200, to an infusion line 3 which may extend from the syringe 2 towards a patient for infusing the medical liquid to the patient.

For installing the syringe 2 on the receptacle 11 of the infusion device 1, the cylindrical tube 20 of the syringe 2 is placed in the receptacle 11 and is mechanically connected to the housing 10 by means of a fixation device 110. By means of the fixation device 110, for example constituted by a releasable clamp element, the cylindrical tube 20 is secured within the receptacle 11 such that the cylindrical tube 20 is held in position on the receptacle 11.

The syringe 2 comprises a piston 21 which, for delivering medical fluid contained in the cylindrical tube 20, can be pushed into the cylindrical tube 20 in a pushing direction P. For this, the infusion device 1 comprises a pusher device 12 movably arranged within a guide device 120 and connected to a drive mechanism (which subsequently shall be described with relation to FIGS. 2 and 3) via a connecting rod 121.

For operating the infusion device 1, the syringe 2 is installed on the infusion device 1 and the pusher device 12 is (manually) moved towards a piston head 210 of the piston 21 until the pusher device 12 comes into abutment with the piston head 210. For performing an infusion process the pusher device 12 is then electrically moved in the pushing direction P to move the piston 21 into the cylindrical tube 20 for delivering the medical fluid contained in the cylindrical tube 20 via the infusion line 3 towards the patient.

The pusher device 12 is driven by a drive mechanism, which, according to one embodiment, is schematically illustrated in FIG. 2. The drive mechanism comprises a drive element 13, which is connected to the pusher device 12 we a connecting rod 121 in a mechanically fixed manner such that by moving the drive element 13 the pusher device 12 is moved along the pushing direction P. The drive element 13 is movable within the housing 10 along the pushing direction P and, via a clutching device 130, is (releasably) connected to a driving rod 14 having a screw thread 140.

A schematic view of an embodiment of the clutching device 130 is shown in FIG. 3. The clutching device comprises two clutch elements 130 which each are pivotably connected, about an associated pivot axis 134, to a frame member 131 of the drive element 13. The clutch elements 130 each are shaped as a half nut and comprise a screw thread 132 by which they may engage with the screw thread 140 of the driving rod 14.

In a clutched state, as illustrated in FIG. 3, the clutch elements 130 are pivoted towards each other in a clutching direction C such that they receive the driving rod 14 in between them and engage with the screw thread 140 of the driving rod 14. To release the engagement, the clutch elements 130 are pivoted opposite to the clutching direction C away from one another, such that they disengage from the screw thread 140 of the driving rod 14 and hence release the connection between the drive element 13 and the driving rod 14.

During regular infusion operation of the infusion device 1 the clutch device is in the clutched state in which the clutch elements 130 engage with the screw thread 140 of the driving rod 14. The driving rod 14, at one end, is connected to an electric drive motor 141 and at the other end is received in a bearing 142 such that, driven by the electric drive motor 141, the driving rod 14 can be rotated about an axis of rotation R1. By rotating the driving rod 14, the drive element 13 (due to the engagement of the clutch elements 130 with the screw thread 140 of the driving rod 14) is longitudinally moved along the driving rod 14, and by the movement of the drive element 13 the pusher device 12 pushes the piston 21 in the pushing direction P into the cylindrical tube 20 of the syringe 2.

The drive element 13 is operatively connected to a brake device 16 having a threaded spindle 160 which is rotatable, within bearings 161, about a rotational axis R2. The drive element 13 comprises an engagement opening 133 having a screw thread therein which engages with a screw thread of the threaded spindle 160. A longitudinal movement of the drive element 13 along the pushing direction P hence causes, due to the engagement, the threaded spindle 160 to be rotated about the rotational axis R2, which generally may be possible at low force if the screw thread of the threaded spindle 160 has a comparatively large pitch.

The threaded spindle 160, at one end, is associated with a brake 162 constituted for example by an electromagnetic brake. If the brake 162 is activated, it blocks a rotation of the threaded spindle 160 about its rotational axis R2. If the threaded spindle 160 is not able to rotate, the drive element 13 cannot move along the threaded spindle 160 such that the drive element 13 is held in position and hence is braked by the brake device 16. If the brake 162 in contrast is deactivated, the threaded spindle 160 is allowed to rotate, such that the drive element 13 is not braked and may be moved longitudinally along the threaded spindle 160.

The operation of the infusion device 1 is controlled by means of a control device 17. In particular, the control device 17 acts onto the electric drive device 141 to rotate the driving rod 14, and the control device 17 acts onto the brake 162 to switch the brake device 16 between its activated and its deactivated state.

The clutch device implemented by the clutch elements 130 is actuatable by means of an actuation device 15, for example in the shape of a lever. Herein, the lever may be manually pressed to unclutch the clutch elements 130 from the driving rod 14, and may be released in order to revert the clutching device to its clutched state.

The drive mechanism as schematically illustrated in FIGS. 2 and 3 may, in one embodiment, be implemented by a mechanism as it is described in US 2012/0215170 A1, which shall be incorporated by reference herein.

In addition, sensing devices 170, 171 are provided which serve to monitor an actuation state of the actuation device 15 and a contact between the pusher device 12 and the piston head 210 of the piston 21.

In particular, a first sensing device 170 detects whether the clutching device is actuated to its unclutched state or its clutched state. The first sensing device 170 can for example be implemented by a mechanical switch, for example a micromechanical switch, for monitoring a position of a lever of the actuation device 15.

A second sensing device 171 serves to detect whether the pusher device 12 is in contact with the piston head 210 of the piston 21 and may be implemented for example by a force sensor, such as piezoelectric sensor, or by a mechanical switch, for example a micromechanical switch.

The sensing devices 170, 171 both issue sensor signals which are fed to the control device 17 and may be used for controlling the operation of the infusion device 1.

As said, for installing a syringe 2 on the infusion device 1 the pusher device 12 is manually moved such that it comes into contact with the piston 21. For this, the clutching device is activated by means of the activation device 15 to its unclutched state, such that the drive element 13 can freely be moved along the driving rod 14. Once the pusher device 12 has come into contact with the piston head 210 of the piston 21, the clutching device is manually brought into engagement with the driving rod 14 by releasing the lever of the actuation device 15.

In addition, during operation of the infusion device it is conceivable that a user may want to perform a manual bolus by manually pushing the pusher device 12 in the pushing direction P to push the piston 21 into the cylindrical tube 20. For this, the clutching device is unclutched such that the pusher device 12 is manually movable, and, after the manual bolus has been performed, is manually reverted to its clutched state such that the regular infusion operation may resume.

As shown in FIG. 4A-4C to 6A, 6B it may occur, within conventional systems, that the transition of the clutching device into the clutched state may cause a (small) lateral movement of the drive element 13 relative to the driving rod 14. This may be undesirable, because this may lead, dependent on the direction of the movement, to a gap in between the pusher device 12 and the piston 21 (causing a delay during startup of a subsequent infusion operation) or an unwanted bolus due to the pusher device 12 unintentionally pushing the piston 21 into the cylindrical tube 20.

Figure 4B:
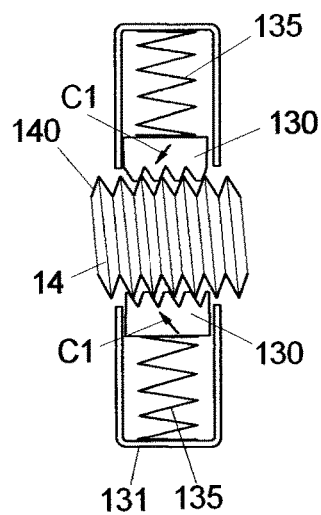
Figure 4C:
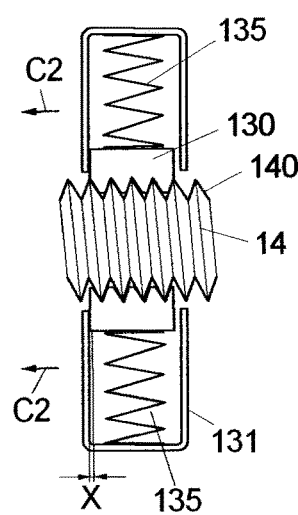

If for example, as illustrated in FIG. 4A to 4C, the clutch elements 130, placed movably within the frame member 131 of the drive element 13 and being pretensioned by means of spring elements 135 towards their clutched state, are actuated to come into engagement with the screw thread 140 of the driving rod 14, they may come into contact, with their threads 132, with flanks of the screw thread 140 of the driving rod 14 and may slide, as shown in FIG. 4B, in a direction C1 into engagement with the screw thread 140 of the driving rod 14. This may lead to a forward movement of the drive element 13 in a direction C2, and may lead to an unwanted bolus because the forward movement in the direction C2 may cause the pusher device 12 to push against the piston 21 and hence to deliver an amount of liquid to the patient.

Figure 5A:
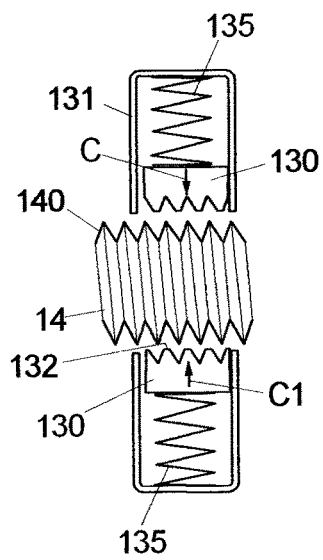
FIG. 5A to 5C show a second situation while actuating the clutching device to assume the clutched state.
Figure 5B:
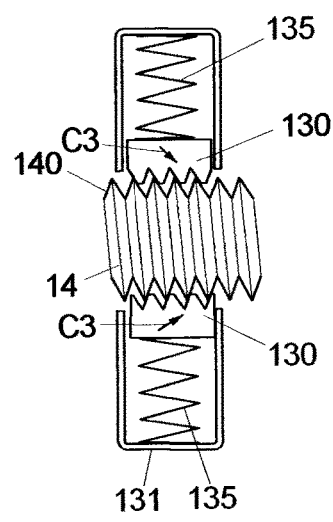
Figure 5C:
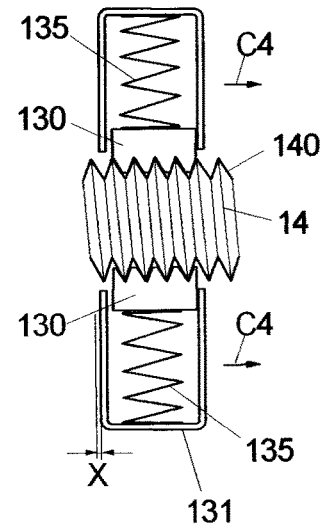

If, in another situation as illustrated in FIG. 5A to 5C, the clutch elements 130, when moved to come into engagement with the screw thread 140 of the driving rod 14, come into contact with opposite flanks of the screw thread 140, the clutch elements 130 may slide in a direction C3 (FIG. 5B) into engagement with the screw thread 140, causing a backward movement of the drive element 13 in a direction C4, as illustrated in FIG. 5C. This may cause the pusher device 12 to be moved opposite to the pushing direction P and hence away from the piston head 210 of the piston 21, such that a gap between the pusher device 12 and the piston head 210 occurs, possibly causing a delay during a subsequent startup of an infusion operation.

In an unlikely scenario, illustrated in FIGS. 6A and 6B, the clutch elements 130 may even not come into engagement with the screw thread 140 of the driving rod 14 at all, if the clutch elements 130 come to rest at tooth crests of the screw thread 140, as illustrated in FIG. 6B.

Hence, the actuation of the clutch elements 130 to come into engagement with the driving rod 14, within conventional systems, may lead to an unwanted movement of the drive element 13, or may lead to an incomplete engagement.

In order to avoid or at least reduce an unwanted movement of the drive element 13 when the clutching device is brought into its clutched state and to ensure a reliable engagement between the clutch elements 130 and the screw thread 140 of the driving rod 14, the control device 17 is constituted to perform a control sequence, which shall be described subsequently according to FIG. 7A-7C to 9A, 9B.

FIG. 7A to 7C depict a scenario in which the clutch elements 130 are (initially) unclutched in order to allow a manual movement of the pusher device 12 together with the drive element 13 in order to bring the pusher device 12 into contact with the piston 21 during installation of the syringe 2 on the infusion device 1. Hence, at the beginning the drive element 13, as depicted in FIG. 7A, is movable relative to the housing 10 along the pushing direction P. The brake device 16 is in its deactivated state and hence does not hinder a movement of the drive element 13.

If, during the installation process of the syringe 2 on the infusion device 1, the second sensing device 171 detects that the pusher device 12 has come into contact with the piston head 210 of the piston 21, the control device 17 causes the brake device 16 to be activated such that the drive element 13 can no longer be moved relative to the threaded spindle 160 and hence is fixedly held in the housing 10. This is illustrated in FIG. 7B.

If a user now activates the actuation device 15 for example by a releasing a lever of the actuation device 15, the clutch elements 130, under the mechanical pretensioning force of the spring elements 135, approach the driving rod 14, wherein the engagement between the clutch elements 130 and the screw thread 140 of the driving rod 14 may at this point not be complete. However, because the drive element 13 is held in position by means of the brake device 16, a movement of the drive element 13 relative to the housing 10 is prevented.

To cause the clutch elements 130 to fully engage with the screw thread 140 of the driving rod 14, the control device 17 now performs a control sequence by repeatedly actuating the electric drive motor 141 to rotate the driving rod 14.

First, as illustrated in FIG. 9A, the driving rod 14 is rotated in a first rotational direction D1, corresponding to a backward movement E1 (which would cause a backward travel in the direction E1 of the drive element 13 in normal operation). The rotation of the driving rod 14 takes place for a predetermined time or for a predetermined angle of rotation, which may depend on the pitch of the screw thread 140 of the driving rod 14 and is chosen such that the clutch elements 130 may fully slide into engagement with the screw thread 140 of the driving rod 14. Because the drive element 13 still is mechanically held in position by the brake device 16, this takes place at no lateral movement of the drive element 13.

The control device 17 then causes the electric drive device 141 to rotate the driving rod 14 in an opposite, second rotational direction D2 corresponding to a forward movement in the direction E2 (which would cause a forward travel in the direction E2 of the drive element 13 in normal operation). This forward movement in the direction E2 coincides with the pushing direction P and serves to overcome a play X (see for example FIG. 4C) which the clutch elements 130 may have relative to the frame member 131 of the drive element 13.

At the end of the control sequence, as shown in FIG. 9C, the clutch elements 130 are in complete engagement with the screw thread 140 of the driving rod 14 and furthermore abut the frame member 131 of the drive element 13 in the pushing direction P. Now the brake device 16 is deactivated such that a regular infusion operation may start by rotating the driving rod 14 in the second rotational direction D2 and by hence moving the drive element 13 forward within the housing 10 in the pushing direction P.

By means of the control sequence a complete engagement between the clutch elements 130 and the driving rod 14 is achieved without a lateral movement of the drive element 13. Hence, the engagement of the clutch elements 130 with the driving rod 14 does not cause a gap between the pusher device 12 and the piston head 210 of the piston 21, and does not cause an unwanted bolus.

Furthermore, by means of the control sequence a play X between the clutch elements 130 and the frame member 131 of the drive element 13 is removed, such that the infusion process may start without a delay (which otherwise may occur because the play X must be overcome).

The control sequence may also be carried out after a manual bolus has been performed, as it is illustrated in FIGS. 8A and 8B.

For performing a manual bolus, the clutch elements 130 are unclutched from the driving rod 14 such that the pusher device 12 together with the drive element 13 may be moved in the pushing direction P to cause a bolus to be infused to the patient. This is illustrated in FIG. 8A.

If the manual bolus has been performed, the actuation device 15 is activated for example by releasing a lever such that the clutch elements 130 are approached to the driving rod 14 to engage with the screw thread 140, as it is illustrated in FIG. 8B. If this is detected by the first sensing device 170, the control device 17 causes the brake device 16 to be activated such that the drive element 13 is fixedly held relative to the housing 10 and can no longer be moved.

Starting from this situation (which resembles the situation in FIG. 7C after installation of the syringe 2 on the infusion device 1), the control sequence according to FIGS. 9A to 9C is carried out, as it has been explained above.

By means of the device and the method described herein the installation of a syringe 2 on an infusion device 1 can be carried out in a semi-automatic fashion in that the pusher device 12 is manually brought into contact with the piston head 210 of the piston 21 of the syringe 2, and complete engagement between the clutch elements 130 and the driving rod 14 is ensured by an automatic control sequence controlled by the control device 17. This allows for a fast installation procedure as well as a reliable clutching engagement, without the risk for a gap in between the pusher device 12 and the piston head 210 after installation or an unwanted bolus.

The device and method furthermore allow to perform a manual bolus, and to reliably establish a clutching engagement after the bolus has been given, without the risk for a gap in between the pusher device 12 and the piston head 210 after re-establishing the clutching or an unwanted bolus.

The invention is not limited to the embodiments described above, but may be implemented in an entirely different fashion.

In particular, the brake device may have an entirely different shape and may be constituted by a brake other than an electromagnetic brake.

Infusion devices of the kind described herein may serve different purposes and may be constituted to receive syringes of different shape and different size. An infusion device of this kind may in particular not be limited to a particular type of syringe as it may be described herein.

LIST OF REFERENCE NUMERALS

1 Infusion device
10 Housing

11 Receptacle
110 Fixation device
12 Pusher device
120 Guide device
121 Connecting rod
13 Drive element
130 Clutch element
131 Frame member
132 Screw thread
133 Engagement opening
134 Pivot axis
135 Spring element
14 Driving rod (spindle)
140 Screw thread
141 Drive motor
142 Bearing
15 Actuation device (handle)
16 Brake device
160 Threaded spindle
161 Bearing
162 Brake
17 Control device
170, 171 Sensing device
2 Syringe
20 Cylinder tube
200 Connector
21 Piston
210 Piston head
3 Infusion line
C Clutching direction
C1-C4 Direction
D1, D2 Direction of rotation
E1, E2 Direction
P Pushing direction
R1, R2 Axis of rotation
X Play

The invention claimed is:

1. An infusion device for administering a medical fluid to a patient, comprising:
a housing,
a receptacle arranged on the housing for receiving a syringe,
a pusher device movable in a pushing direction for acting onto a piston of the syringe received on the receptacle,
a drive element connected to the pusher device, the drive element being longitudinally movable relative to the housing for moving the pusher device along the pushing direction,
a driving rod having a screw thread and being rotatable about a rotational axis,
an electric drive device for rotating the driving rod,
a clutching device connected to the drive element and being actuatable, by an actuation device, to engage, in a clutched state, with the screw thread of the driving rod for translating a rotational movement of the driving rod into a longitudinal movement of the drive element along the driving rod, and to disengage, in an unclutched state, from the driving rod,
a brake device configured to act, in an activated state, onto the drive element for braking the drive element relative to the housing and to allow, in a deactivated state, a longitudinal movement of the drive element relative to the housing,
a control device to control the electric drive device and the brake device, and
a sensing device for detecting an actuation state of the clutching device,
wherein the control device is configured, when the sensing device detects that the clutching device is actuated to change from the unclutched state to the clutched state, to perform a control sequence during which the control device controls the electric drive device to rotate the driving rod for a predetermined duration or for a predetermined angle of rotation while the brake device is in the activated state, and
wherein the control device is configured to actuate the brake device to assume the activated state when the sensing device detects that the clutching device is actuated, by the actuation device, to change from the unclutched state to the clutched state.

2. The infusion device according to claim 1, wherein the control device is configured, when performing the control sequence, to control the electric drive device to rotate the driving rod in a first rotational direction for a first predetermined duration or for a first predetermined angle of rotation and to subsequently rotate the driving rod in a second rotational direction opposite the first rotational direction for a second predetermined duration or for a second predetermined angle of rotation.

3. The infusion device according to claim 2, wherein the first rotational direction corresponds to a backwards rotation for moving the drive element in a direction opposite to the pushing direction, and the second rotational direction corresponds to a forward rotation for moving the drive element in the pushing direction.

4. The infusion device according to claim 1, wherein the control device is configured to control the brake device to assume the deactivated state after the driving rod has been rotated.

5. The infusion device according to claim 1, wherein the clutching device comprises a pair of clutch elements movably arranged on the drive element and each having a screw thread for engaging with the screw thread of the driving rod.

6. The infusion device according to claim 5, wherein the clutch elements are pivotably arranged on a frame member of the drive element.

7. The infusion device according to claim 1, wherein the control device is configured, when performing the control sequence, to control the electric drive device to rotate the driving rod for the predetermined duration or for the predetermined angle of rotation in one or both rotational directions in either order.

\* \* \* \* \*